US009333024B2

(12) United States Patent
Woloszko et al.

(10) Patent No.: US 9,333,024 B2
(45) Date of Patent: May 10, 2016

(54) ELECTROSURGICAL SYSTEMS AND METHODS

(71) Applicant: ArthroCare Corporation, Austin, TX (US)

(72) Inventors: Jean Woloszko, Austin, TX (US); Duane W. Marion, Pleasanton, CA (US); Johnson E. Goode, Austin, TX (US); George Morrison, Austin, TX (US); David Yuan, Cedar Park, TX (US)

(73) Assignee: ArthroCare Corporation, Austin, TX (US)

( * ) Notice: Subject to any disclaimer, the term of this patent is extended or adjusted under 35 U.S.C. 154(b) by 0 days.

(21) Appl. No.: 14/238,799

(22) PCT Filed: Mar. 7, 2013

(86) PCT No.: PCT/US2013/029501
§ 371 (c)(1),
(2) Date: Feb. 13, 2014

(87) PCT Pub. No.: WO2014/137342
PCT Pub. Date: Sep. 12, 2014

(65) Prior Publication Data
US 2014/0336630 A1 Nov. 13, 2014

(51) Int. Cl.
*A61B 18/12* (2006.01)
*A61B 18/10* (2006.01)
(Continued)

(52) U.S. Cl.
CPC ............ *A61B 18/10* (2013.01); *A61B 18/1206* (2013.01); *A61B 18/1402* (2013.01); *A61B 18/148* (2013.01); *A61B 18/1482* (2013.01); *A61B 2018/00577* (2013.01); *A61B 2018/00636* (2013.01); *A61B 2018/00702* (2013.01);
(Continued)

(58) Field of Classification Search
CPC .......... A61B 2018/00583; A61B 2018/00557; A61B 2018/00744; A61B 2018/00767; A61B 2018/00702; A61B 2018/00875; A61B 2018/1472
See application file for complete search history.

(56) References Cited

U.S. PATENT DOCUMENTS

| 5,167,658 | A | 12/1992 | Ensslin | 606/34 |
| 5,342,357 | A | 8/1994 | Nardella | 606/40 |

(Continued)

FOREIGN PATENT DOCUMENTS

| EP | 1917927 | 5/2008 | A61B 18/12 |
| WO | 2015-122969 | 8/2015 | A61B 18/12 |

OTHER PUBLICATIONS

International Search Report and Written Opinion for PCT/US2013/029501 12pgs, Nov. 20, 2013.

(Continued)

*Primary Examiner* — Ronald Hupczey, Jr.

(57) ABSTRACT

System and methods of an electrosurgical controller having multiple modes of operation that are configured for treatment of a specific targeted tissue type and the electrosurgical effect desired where the treatment and effect are provided by a single controller and an electrosurgical probe. The electrosurgical controller includes an integrated fluid control apparatus or pump where activation of the controller allows for selective energy delivery and corresponding fluid volume flow rates. The electrosurgical probe includes a fluid transport lumen and is in communication with the controller and the pump for operation of the probe in the various user selected modes with accompanying energy delivery and fluid control directed to the desired treatment and surgical effect.

17 Claims, 6 Drawing Sheets

(51) Int. Cl.
*A61B 18/14* (2006.01)
*A61B 18/00* (2006.01)

(52) U.S. Cl.
CPC .............. *A61B2018/00744* (2013.01); *A61B 2018/00755* (2013.01); *A61B 2018/00875* (2013.01); *A61B 2018/122* (2013.01); *A61B 2218/002* (2013.01); *A61B 2218/007* (2013.01)

(56) References Cited

U.S. PATENT DOCUMENTS

| | | | | |
|---|---|---|---|---|
| 5,569,188 | A * | 10/1996 | Mackool | A61F 9/00745 604/119 |
| 6,142,992 | A | 11/2000 | Cheng et al. | 606/34 |
| 6,780,178 | B2 | 8/2004 | Palanker et al. | 606/34 |
| 6,780,184 | B2 | 8/2004 | Tanrisever | 606/45 |
| 8,192,424 | B2 | 6/2012 | Woloszko | 606/40 |
| 2006/0171848 | A1 | 8/2006 | Roche et al. | 422/98 |
| 2007/0083193 | A1 | 4/2007 | Werneth et al. | 606/41 |
| 2007/0129716 | A1 | 6/2007 | Daw et al. | 606/34 |
| 2007/0179495 | A1 | 8/2007 | Mitchell et al. | 606/41 |
| 2010/0100112 | A1 | 4/2010 | Kauker et al. | 606/180 |
| 2010/0121317 | A1 | 5/2010 | Lorang et al. | 606/32 |
| 2011/0137308 | A1 * | 6/2011 | Woloszko | A61B 18/1485 606/41 |
| 2011/0208177 | A1 | 8/2011 | Brannan | 606/33 |
| 2013/0006237 | A1 | 1/2013 | Werner | 606/40 |
| 2014/0257269 | A1 | 9/2014 | Woloszko et al. | 606/34 |

OTHER PUBLICATIONS

Search Report and Written Opinion PCT/US2014/072753 13 pgs Apr. 2, 2015.

* cited by examiner

ELECTROSURGICAL SYSTEMS AND METHODS

BACKGROUND

Electrosurgical systems are used by physicians to perform specific functions during surgical procedures. Within these procedures, it may be necessary to treat more than one type of tissue or to create more than one manner of tissue effect. Existing electrosurgical systems are typically designed with limited functionality, and are not always particularly effective for treating varying tissue types. In the event that a procedure requires multiple types of tissue to be treated, the use of a single device may produce poor results in certain aspects of the procedure and necessitate that a user have available or switch between several surgical instruments to obtain the desired surgical result. For example, particular electrosurgical procedures in the knee or shoulder may require several different modes of operation to effectively treat different types of tissue. Each mode may utilize a different amount of energy, and in the related art each mode may involve the use of different electrosurgical wands and different electrosurgical controllers. In some cases, a surgeon may forgo use of the correct wand and/or electrosurgical controller to reduce expenses of the procedure, when better clinical results may have been achieved using multiple electrosurgical wands.

Any advance that makes treatment easier for the surgeon, and achieves better results, would provide a competitive advantage.

BRIEF DESCRIPTION OF THE DRAWINGS

For a detailed description of exemplary embodiments, reference will now be made to the accompanying drawings in which.

NOTATION AND NOMENCLATURE

Figure 1:
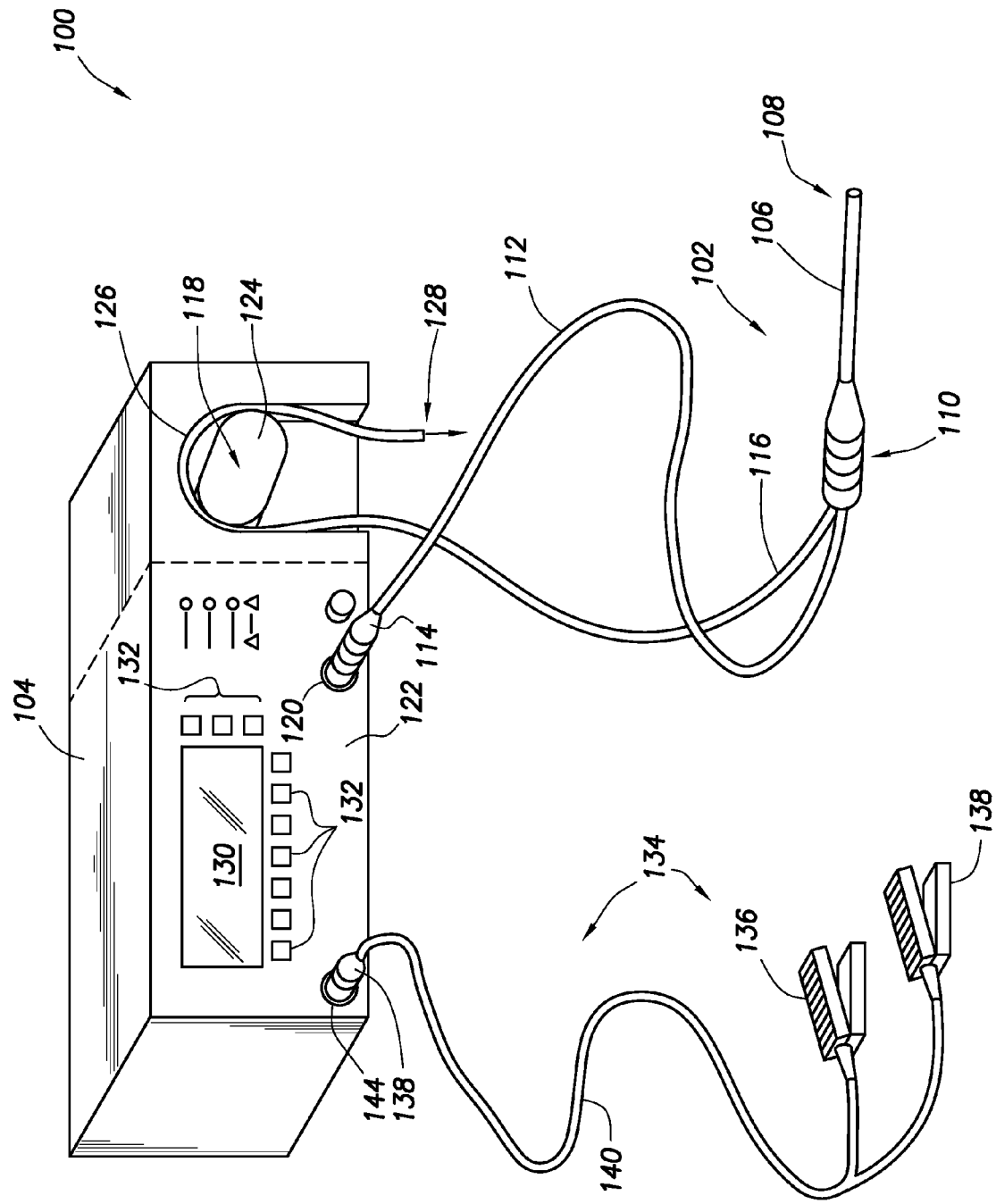
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with a plasma.

"Mode of ablation" shall refer to one or more characteristics of an ablation. Lack of ablation (i.e., a lack of plasma) shall not be considered an "ablation mode." A mode which performs coagulation shall not be considered an "ablation mode."

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Electric motor" shall include alternating current (AC) motors, direct current (DC) motors, as well as stepper motors.

"Controlling flow of fluid" shall mean controlling a volume flow rate. Control of applied pressure to maintain a set point pressure (e.g., suction pressure) independent of volume flow rate of liquid caused by the applied pressure shall not be considered "controlling flow of fluid." However, varying applied pressure to maintain a set point volume flow rate of liquid shall be considered "controlling flow of fluid".

"Substantially", in relation to exposed surface areas of electrodes, shall mean that exposed surface areas as between two electrodes are same, or differ by no more than twenty five (25) percent.

A fluid conduit said to be "within" an elongate shaft shall include not only a separate fluid conduit that physically resides within all or a portion of an internal volume of the elongate shaft, but also situations where the internal volume of the elongate shaft is itself the fluid conduit or where a separate fluid conduit is connected along the length of or to a portion of the elongate shaft.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The various embodiments are directed to electrosurgical methods and related electrosurgical systems. In particular, the various embodiments are directed to an electrosurgical system having multiple modes of operation that are configured for treatment of a specific targeted tissue type or electrosurgical effect desired, and implemented by a single electrosurgical wand and a single electrosurgical controller. In example embodiments, the multiple modes of operation are implemented by a single active electrode on the electrosurgical wand. The specification first turns to an illustrative system to orient the reader.

FIG. 1 illustrates an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle or proximal end 110, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in the figure), but in any event the peristaltic pump is operatively coupled to the controller 104.

The peristaltic pump 118 comprises a rotor portion 124 (hereafter just "rotor 124") as well as a stator portion 126 (hereafter just "stator 126"). The flexible tubular member 116 couples within the peristaltic pump 118 between the rotor 124 and the stator 126, and movement of the rotor 124 against the flexible tubular member 116 causes fluid movement toward the discharge 128. While the illustrative peristaltic pump 118 is shown with a two-head rotor 124, varying types of peristaltic pumps 118 may be used (e.g., a five head peristaltic pump). In the context of the various embodiments, the peristaltic pump 118 creates a volume-controlled aspiration from a surgical field at the distal end 108 of the want 102, with the control based on a speed of the rotor 124, as commanded by the controller 104.

Still referring to FIG. 1, a display device or interface device 130 is visible through the enclosure 122 of the controller 104, and in some embodiments a user may select operational modes of the controller 104 by way of the interface device 130 and/or related buttons 132. For example, using one or more of the buttons 132 the surgeon may select among ablation modes, such as: a low mode which may be used for removal of portions of cartilage; a medium mode which may be used for removal of meniscus; a high mode for aggressive removal of tissue; and a vacuum mode for removal free floating and/or trapped tissue. The various modes of operation are discussed more thoroughly below.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102, and more specifically for control of energy in an ablation mode. Further, pedal device 138 may be used to control and/or set the mode of ablation of the electrosurgical system. For example, actuation of pedal device 138 may switch between energy levels created by the controller 104 and aspiration volume created by the peristaltic pump 118. In certain embodiments, control of the various operational or performance aspects of controller 104 may be activated by selectively depressing finger buttons located on handle 110 of wand 102.

The electrosurgical system 100 of the various embodiments may have a variety of modes of operation which employ Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is energized to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

The inventors now present a theoretical underpinning to explain how multiple modes of operation may be implemented with a single wand 102 and a single controller 104. However, the theoretical basis is presented merely as one possible explanation, and shall not be read as a limitation on the operation of the various embodiments. Another theoretical basis may be equivalently proffered, and attempting to explain operation of a device using a different theoretical basis shall not obviate whether such a device falls within the appended claims. In particular, the electrode circuit, including the plasma created in operational relationship to an active electrode of a wand, the fluid between the active and return electrode, and the electrode-fluid interface, has or presents a certain amount of impedance to the flow of energy away from the active electrode toward a return electrode. The impedance presented by the electrode circuit may be dependent on many factors, including but not limited to the thickness and volume of the plasma itself, the surface area of the active electrode not covered by a vapor layer and directly in contact with the conductive fluid, and the volume flow of fluid and/or gasses away from the location of the plasma.

In related-art devices, only the vacuum pressure used for aspiration is controlled (e.g., the vacuum available at wall socket connections in a hospital operating room). However, the vacuum available at a wall socket connection may be highly variable from room to room, and in many cases within the same room over time. Moreover, control of vacuum pressure applied does not imply a controlled volume of aspiration. Thus, while related-art devices may control vacuum pressure (or may specify a preferred vacuum pressure), they do not control volume flow rate of the aspiration.

The various modes of operation are implemented, at least in part and in certain embodiments, by controlling the flow of fluid during the aspiration, rather than merely controlling the applied vacuum pressure. In some embodiments, and as illustrated in FIG. 1, controlling the flow of fluid is by way of a peristaltic pump 118, but other mechanisms to control flow may be equivalently used, including pressure modulation. In part by controlling the flow of fluid of the aspiration, the impedance at the electrode circuit may be at least partially controlled. Though other parameters also may also influence impedance, the inventors have found that lower volume flow of fluid of the aspiration results in higher electrode circuit impedance by generating a larger plasma and having less of the active electrode in direct contact with the conductive fluid and thus less energy dissipation, and higher volume flow of fluid of the aspiration results in lower impedance and thus more energy dissipation. Higher volume flow reduces the size of the plasma and therefore increases the strength of the electrical field within the plasma.

The inventors have found that the relationship of the volume of flow of fluid of the aspiration to energy dissipation is counter to the prevailing understanding. That is, related-art devices and methods operate under the assumption that a generally high flow rate more rapidly carries away energy and thus reduces thermal aspects of the ablation. By contrast, the inventors have found that high volume flow of aspiration tends to cause higher energy dissipation overall. That is, a high volume flow rate makes the impedance of the electrode circuit lower, which lower impedance increases the energy dissipation. Moreover, higher volume flow rates cause the plasma to "flicker". Consider an analogy in the form of a candle. If a candle is burning in a room with very little air movement, the flame may maintain a steady shape, size, and location. However, in the presence of airflow (e.g., a ceiling fan), the flame tends to "flicker". If one considers that during periods of time of plasma collapse (i.e., absence of plasma) greater energy is dissipated in a thermal mode through the surrounding fluid and tissue, "flickering" plasma (plasma which is repeatedly collapsing and re-forming) caused by high volume flow rate may result in more energy dissipation in the tissue and surrounding fluid, rather than less. That is, not only will the "flickering" plasma present a lower average impedance and thus higher energy dissipation, but also the thermal mode that dominates during momentary plasma collapse present in "flicker" causes higher energy dissipation than periods of time when plasma is present.

Accordingly, the embodiments described herein are related to a system wherein the impedance (or RF current applied to an active electrode, which may be used to calculate impedance) at the electrode is monitored and used as a parameter to control the volume flow rate of aspiration in order to control the plasma field in a way that is desirable for a specific tissue type or procedure. For example, if the impedance at the active electrode is observed to decrease at a point during a procedure (possibly indicating plasma instability), the control module of the system may direct the aspiration pump to decrease the aspiration flow rate to enable the plasma field to stabilize. From another perspective, it may be desirable measure the RF current applied to the active electrode and adjust the aspiration fluid flow in order to keep the current at a certain predetermined and desired level associated with the user's operating preference. Additionally, in certain procedures it may be desirable to sacrifice fluid flow in lieu of stabilizing the plasma field in order to reduce heat dissipation at the treatment site and to enhance tissue preservation. Reference is also made to commonly assigned U.S. Pat. No. 8,192,424, entitled "ELECTROSURGICAL SYSTEM WITH SUCTION CONTROL APPARTUS, SYSTEM AND METHOD" the complete disclosure of which is incorporated herein by reference for all purposes. Conversely, it may be desirable in certain procedure types to trade off plasma field stability in order to have higher overall aspiration fluid flow volume in order to remove bubbles and debris from the surgical field.

Based on the theoretical underpinning in the paragraphs above, the various embodiments are directed to systems and related methods implementing at least two modes of operation during an electrosurgical procedure, in some embodiments using a single wand (and in some cases a single active electrode) along with a single controller. In a particular embodiment, four different modes of operation may be implemented, such as: a "low mode" which may be used for the treatment and removal of sensitive tissue like portions of articular cartilage; a "medium mode" which may be used for the treatment and removal of meniscus; a "high mode" for aggressive removal of tissue of any kind; and a "vacuum mode" for removal of free floating and/or trapped tissue. More detail regarding the illustrative modes of ablation is presented below, after a discussion of an illustrative wand 102 and internal components of the controller 104.

Figure 2:
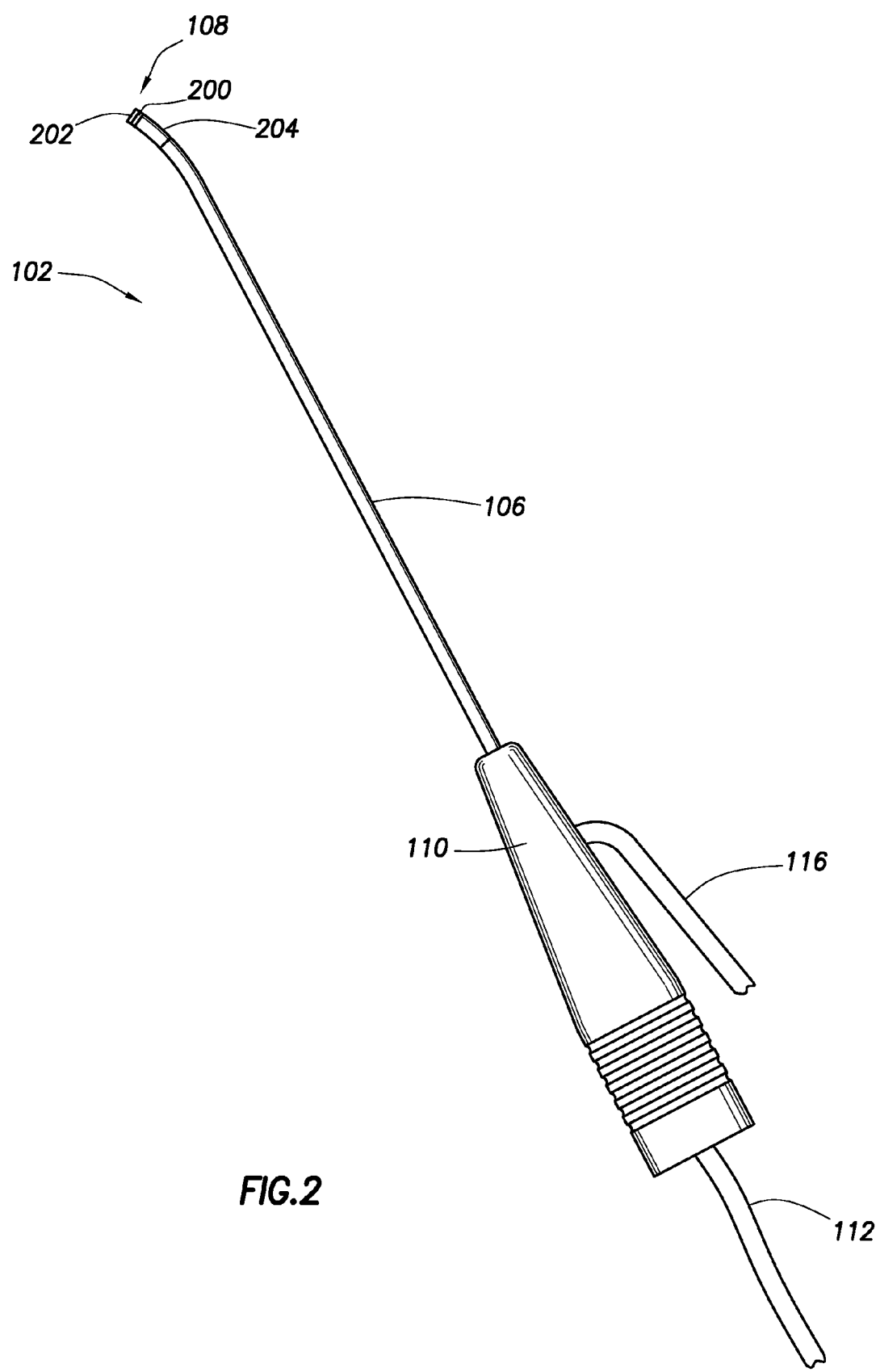
FIG. 2 shows an elevation view of an electrosurgical wand in accordance with at least some embodiments.

FIG. 2 shows an elevation view of wand 102 in accordance with example systems. In particular, wand 102 comprises elongate shaft 106 which may be flexible or rigid, a handle 110 coupled to the proximal end of the elongate shaft 106, and an electrode support member 200 coupled to the distal end of elongate shaft 106. Also visible in FIG. 2 is the flexible tubular member 116 extending from the wand 102 and the multi-conductor cable 112. The wand 102 comprises an active electrode 202 disposed on the distal end 108 of the elongate shaft 106. Active electrode 202 may be coupled to an active or passive control network within controller 104 (FIG. 1) by means of one or more insulated electrical connectors (not shown) in the multi-conductor cable 112. The active electrode 202 is electrically isolated from a common or return electrode 204 which is disposed on the shaft proximally of the active electrode 202, in some example systems within 1 millimeter (mm) to 25 mm of the distal tip. Proximally from the distal tip, the return electrode 204 is concentric with the elongate shaft 106 of the wand 102. The support member 200 is positioned distal to the return electrode 204 and may be composed of an electrically insulating material such as epoxy, plastic, ceramic, silicone, glass or the like. Support member 200 extends from the distal end 108 of elongate shaft 106 (usually about 1 to 20 mm) and provides support for active electrode 202.

Figure 3:
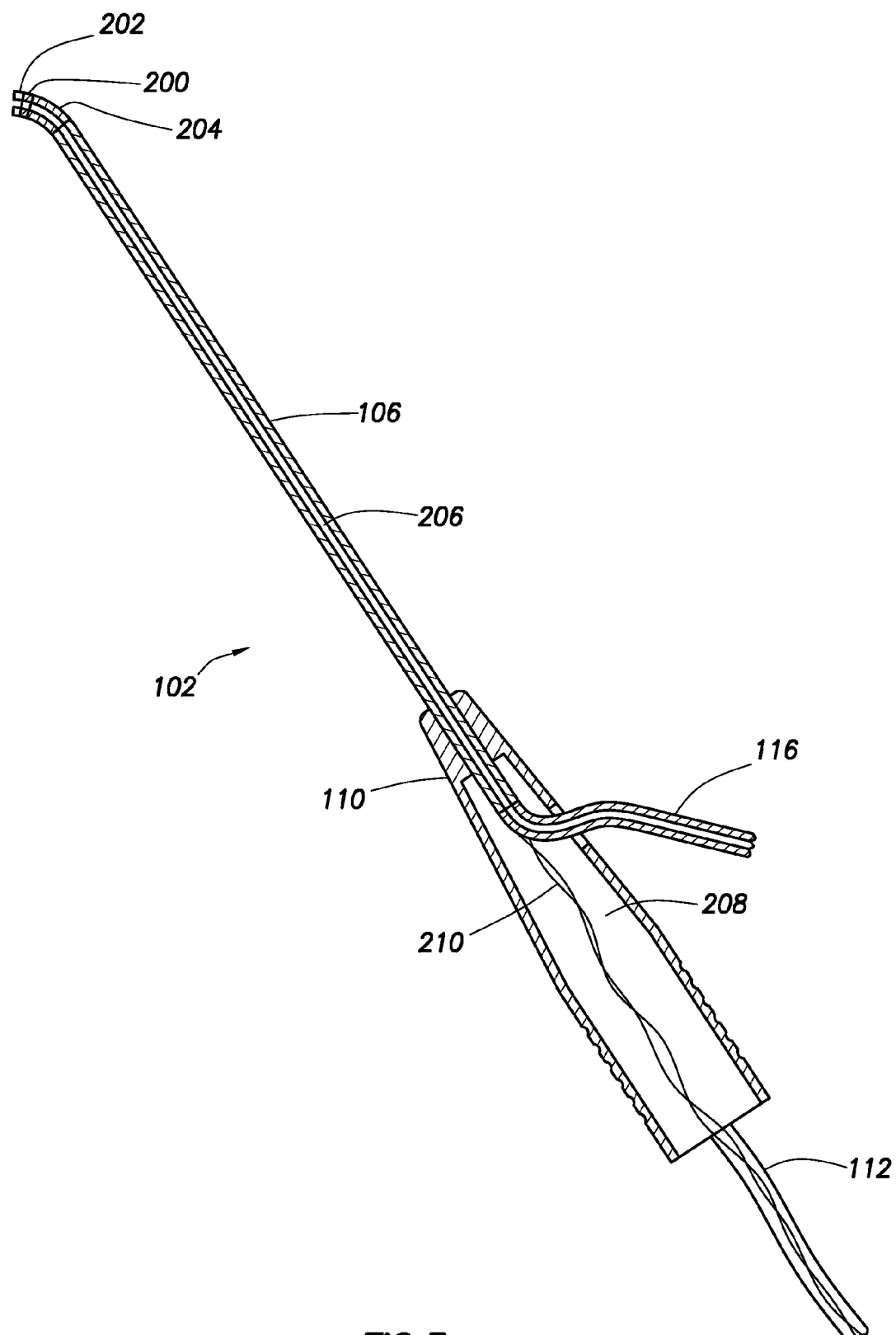
FIG. 3 shows a cross-sectional elevation view of an electrosurgical wand in accordance with at least some embodiments.

FIG. 3 shows a cross-sectional elevation view of the wand 102 in accordance with example embodiments. In particular, wand 102 comprises a suction lumen 206 defined within the elongate shaft 106. In the example wand 102 of FIG. 3, the inside diameter of the elongate shaft 106 defines the section lumen 206, but in other cases a separate tubing within the elongate shaft 106 may define the suction lumen 206. The suction lumen 206 may be used for aspirating excess fluids, bubbles, tissue fragments, and/or products of ablation from the target site proximate to the active electrode 202. Suction lumen 206 extends into the handle 110 and fluidly couples to the flexible tubular member 116 for coupling to the peristaltic pump 118. Handle 110 also defines an inner cavity 208 within which electrical conductors 210 may reside, where the electrical conductors 210 may extend into the multi-conductor cable 112 and ultimately couple to the controller 104. The electrical conductors likewise extend through the elongate shaft and couple, one each, to the return electrode 204 and the active electrode 202, but the electrical conductors 210 are not shown to reside within the elongate shaft 106 so as not to unduly complicate the figure.

Figure 4:
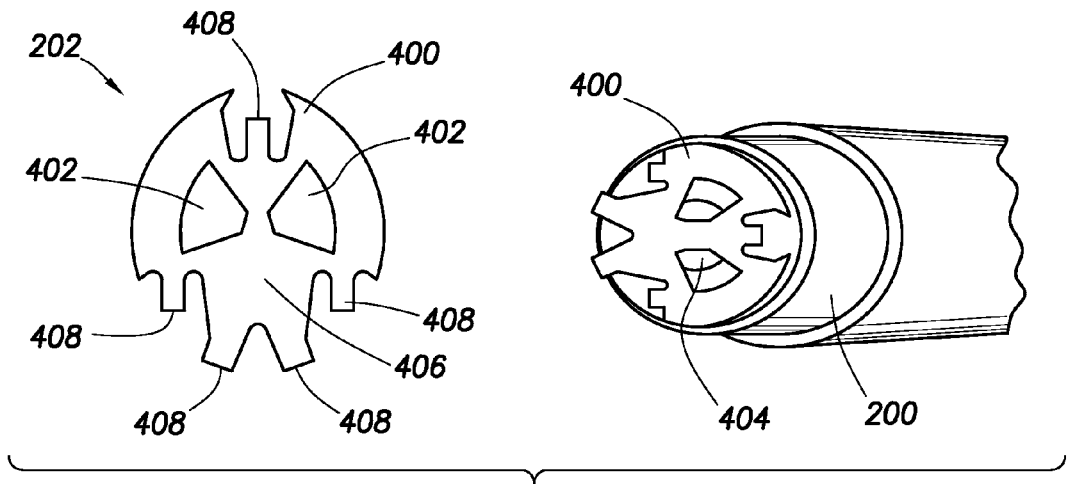
FIG. 4 shows both an elevation view of screen electrode, and a perspective view of a distal end of an electrosurgical wand comprising the screen electrode, in accordance with at least some embodiments.

FIG. 4 shows an elevation view of an example active electrode (on the left), as well as a perspective view of the distal end of wand 102 (on the right), in accordance with example systems. In particular, active electrode 202 may be an active screen electrode 400 as shown in FIG. 4. Screen electrode 400 may comprise a conductive material, such as tungsten, titanium, molybdenum, platinum, or the like. Screen electrode 400 may have a diameter in the range of about 0.5 to 8 mm, in some cases about 1 to 4 mm, and a thickness of about 0.05 to about 2.5 mm, in some cases about 0.1 to 1 mm. Screen electrode 400 may comprise a plurality of apertures 402 configured to rest over the distal opening 404 of suction lumen. Apertures 402 are designed to enable the passage of aspirated excess fluids, bubbles, and gases from the ablation site and are large enough to enable ablated tissue fragments to pass through into suction lumen 206 (FIG. 3). As shown, screen electrode 400 has an irregular shape which increases the edge to surface-area ratio of the screen electrode 400. A large edge to surface-area ratio increases the ability of screen electrode 400 to initiate and maintain a plasma layer in conductive fluid because the edges generate higher current densities, which a large surface area electrode tends to dissipate power into the conductive media.

In the representative embodiment shown in FIG. 4, screen electrode 400 comprises a body 406 that rests over insulative support member 200 and the distal opening 404 to suction lumen 206. Screen electrode 400 further comprises tabs 408, in the example screen electrode 400 of FIG. 4, five tabs 408 are shown. The tabs 408 may rest on, be secured to, and/or be embedded in insulative support member 200. In certain embodiments, electrical connectors extend through insulative support member 200 and are coupled (i.e., via adhesive, braze, weld, or the like) to one or more of tabs 408 in order to secure screen electrode 400 to the insulative support member 200 and to electrically couple screen electrode 400 to controller 104 (FIG. 1). In example systems, screen electrode 400 forms a substantially planar tissue treatment surface for smooth resection, ablation, and sculpting of the meniscus, cartilage, and other tissues. In reshaping cartilage and meniscus, the physician often desires to smooth the irregular and ragged surface of the tissue, leaving behind a substantially smooth surface. For these applications, a substantially planar screen electrode treatment surface provides the desired effect. The specification now turns to a more detailed description of the controller 104.

Figure 5:
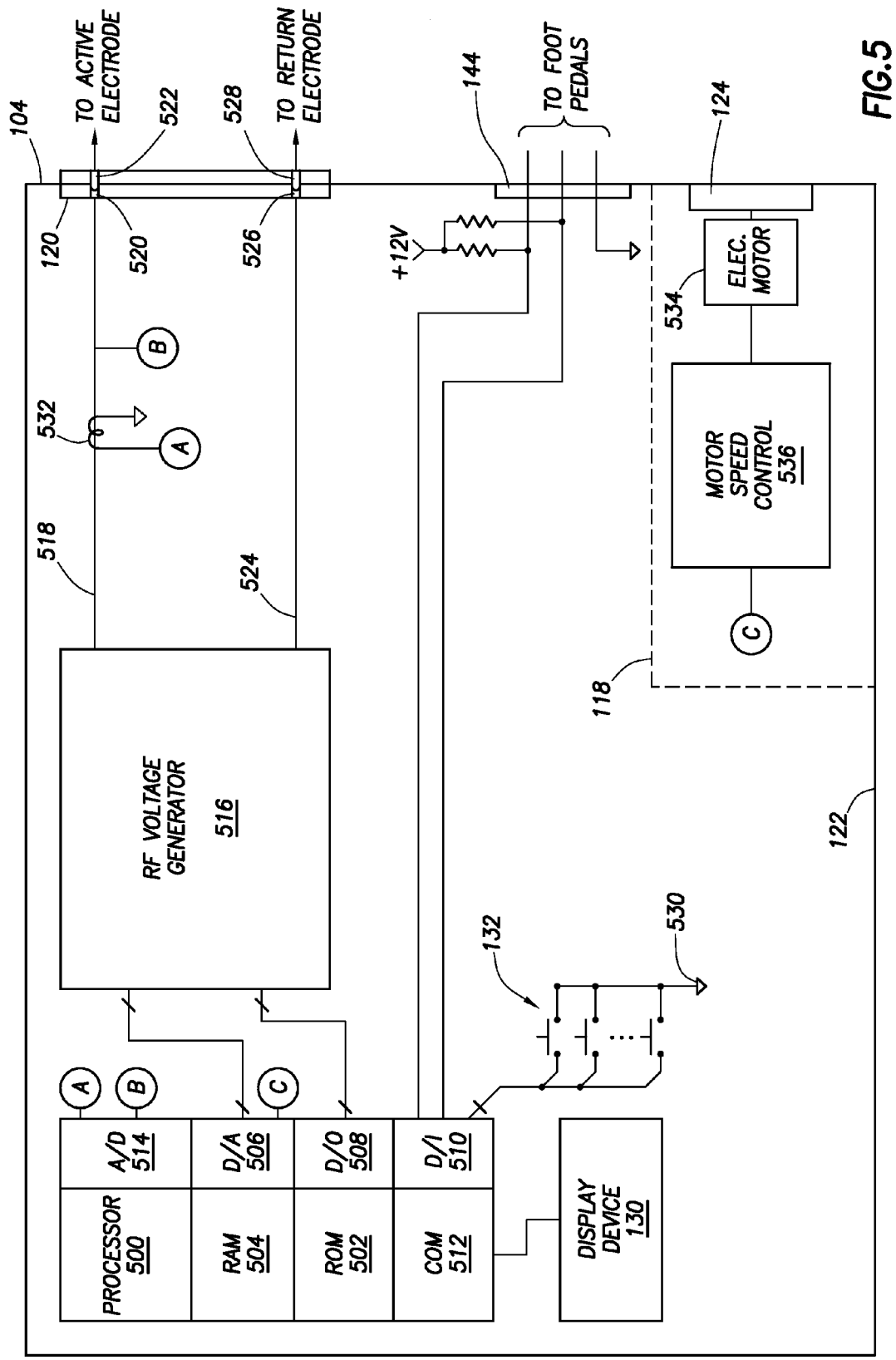
FIG. 5 shows an electrical block diagram of a controller in accordance with at least some embodiments.

FIG. 5 shows an electrical block diagram of controller 104 in accordance with at least some embodiments. In particular, the controller 104 comprises a processor 500. The processor 500 may be a microcontroller, and therefore the microcontroller may be integral with read-only memory (ROM) 502, random access memory (RAM) 504, digital-to-analog converter (D/A) 506, analog-to-digital converter (A/D) 514, digital outputs (D/O) 508, and digital inputs (D/I) 510. The processor 500 may further provide one or more externally available peripheral busses, such as a serial bus (e.g., I$^2$C), parallel bus, or other bus and corresponding communication mode. The processor 500 may further be integral with communication logic 512 to enable the processor 500 to communicate with external devices, as well as internal devices, such as display device 130. Although in some embodiments the processor 500 may be implemented in the form of a microcontroller, in other embodiments the processor 500 may be implemented as a standalone central processing unit in combination with individual RAM, ROM, communication, A/D, D/A, D/O, and D/I devices, as well as communication hardware for communication to peripheral components.

ROM 502 stores instructions executable by the processor 500. In particular, the ROM 502 may comprise a software program that, when executed, causes the controller to implement two or more modes of operation. The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF generator 516), digital outputs 508 (e.g., in some embodiment the RF generator 516), digital inputs 510 (e.g., interface devices such as push button switches 132 or foot pedal assembly 134 (FIG. 1)), communication device 512 (e.g., display device 130).

Voltage generator 516 generates an alternating current (AC) voltage signal that is coupled to active electrode 202 of the wand 102. In some embodiments, the voltage generator defines an active terminal 518 which couples to electrical pin 520 in the controller connector 120, electrical pin 522 in the wand connector 114, and ultimately to the active electrode 202. Likewise, the voltage generator defines a return terminal 524 which couples to electrical pin 526 in the controller connector 120, electrical pin 528 in the wand connector 114, and ultimately to the return electrode 204. Additional active terminals and/or return terminals may be used. The active terminal 518 is the terminal upon which the voltages and electrical currents are induced by the voltage generator 516, and the return terminal 524 provides a return path for electrical currents. It would be possible for the return terminal 524 to provide a common or ground being the same as the common or ground within the balance of the controller 104 (e.g., the common 530 used on push-buttons 132), but in other embodiments the voltage generator 516 may be electrically "floated" from the balance of the controller 104, and thus the return terminal 524, when measured with respect to the common or earth ground (e.g., common 530) may show a voltage; however, an electrically floated voltage generator 516 and thus the potential for voltage readings on the return terminals 524 relative to earth ground does not negate the return terminal status of the terminal 524 relative to the active terminal 518.

The AC voltage signal generated and applied between the active terminal 518 and return terminal 524 by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is much greater at 100 kHz.

The RMS (root mean square) voltage generated by the voltage generator 516 may be in the range from about 5 Volts (V) to 1800 V, in some cases in the range from about 10 V to 500 V, often between about 10 V to 400 V depending on the active electrode size. The peak-to-peak voltage generated by the voltage generator 516 for ablation in some embodiments is a square waveform with a peak-to-peak voltage in the range of 10 V to 2000 V, in some cases in the range of 100 V to 1800 V, in other cases in the range of about 28 V to 1200 V, and often in the range of about 100 V to 320V peak-to-peak.

The voltage and current generated by the voltage generator 516 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of a square wave voltage produced by the voltage generator 516 is on the order of about 50% for some embodiments as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

The voltage generator 516 delivers average power levels ranging from several milliwatts to hundreds of watts per electrode, depending on the mode of ablation and state of the plasma proximate to the active electrode. The voltage generator 516 in combination with the processor 500 are configured to initially set the energy output of the voltage generator 516 (e.g., by controlling output voltage) based on the mode of ablation selected by the surgeon, and while in a selected mode of ablation to make control changes to compensate for changes caused by use of the wand. The control changes are discussed more below after a further discussion of the peristaltic pump 118. A description of various voltage generators 516 can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, entitled "METHOD AND SYSTEM OF AN ELECTROSURGICAL CONTROLLER WITH WAVE-SHAPING", the complete disclosure of which is incorporated herein by reference as if reproduced in full below.

In some embodiments, the various modes of operation implemented, at least in part, by the voltage generator 516 may be controlled by the processor 500 by way of digital-toanalog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator by way of one or more digital output signals from the digital output converter 508, or by way of packet-based communications using the communication device 512 (the communication-based embodiments not specifically shown so as not to unduly complicate FIG. 5).

Still referring to FIG. 5, in some embodiment the controller 104 further comprises a mechanism to sense the electrical current provided to the active electrode. In the illustrative case of FIG. 3, sensing current provided to the active electrode may be by way of a current sense transformer 532. In particular, current sense transformer 532 may have a conductor of the active terminal 518 threaded through the transformer such that the active terminal 518 becomes a single turn primary. Current flow in the single turn primary induces corresponding voltages and/or currents in the secondary. Thus, the illustrative current sense transformer 532 is coupled to the analog-to-digital converter 514 (as shown by the bubble A). In some cases, the current sense transformer may couple directly to the analog-to-digital converter 514, and in other cases additional circuitry may be imposed between the current sense transformer 532 and the analog-to-digital converter 514, such as amplification circuits and protection circuits. The current sense transformer is merely illustrative of any suitable mechanism to sense the current supplied to the active electrode, and other systems are possible. For example, a small resistor (e.g., 1 Ohm, 0.1 Ohm) may be placed in series with the active terminal 518, and the voltage drop induced across the resistor used as an indication of the electrical current. In yet still other cases, current sense circuitry may measure the current in any suitable form, and the measured current values may be provided other than by analog signal, such as by way of packet-based communications over the communication port 512 (not shown so as not to unduly complicate the drawing).

Given that the voltage generator 516 is electrically floated, the mechanism to sense current is not limited to the just the active terminal 518. Thus, in yet still further embodiments, the mechanism to sense current may be implemented with respect to the return terminal 524. For example, illustrative current sense transformer 532 may be implemented on a conductor associated with the return terminal 524.

In some embodiments, the only feedback parameter used by the processor regarding the voltage generator 516 is the electrical current flow. For example, in systems where the voltage generator can accurately produce an output voltage independent of the impedance of the attached load, the processor 500 having set point control for the voltage created by the voltage generator 516 may be sufficient (e.g., to calculate a value indicative of impedance of the plasma proximate the active electrode). However, in other cases, voltage may also be a feedback parameter. Thus, in some cases the active terminal 518 may be electrically coupled to the analog-to-digital converter 514 (as shown by bubble B). However, additional circuitry may be imposed between the active terminal 518 and the analog-to-digital converter 514, for example various step-down transformers, protection circuits, and circuits to account for the electrically floated nature of the voltage generator 516. Such additional circuitry is not shown so as not to unduly complicate the figure. In yet still other cases, voltage sense circuitry may measure the voltage, and the measured voltage values may be provided other than by analog signal, such as by way of packet-based communications over the communication port 512 (not shown so as not to unduly complicate the drawing).

Still referring to FIG. 5, controller 104 in accordance with various embodiments further comprises peristaltic pump 118. The peristaltic pump 118 may reside at least partially within the enclosure 122. The peristaltic pump comprises the rotor 124 mechanically coupled to a shaft of the electric motor 534. In some cases, and as illustrated, the rotor of the electric motor may couple directly to the rotor 124, but in other cases various gears, pulleys, and/or belts may reside between the electric motor 534 and the rotor 124. The electric motor 534 may take any suitable form, such as an AC motor, a DC motor, and/or a stepper-motor. To control speed of the shaft of the electric motor 534, and thus to control speed of the rotor 124 (and the volumetric flow rate at the wand), the electric motor 534 may be coupled to a motor speed control circuit 536. In the illustrative case of an AC motor, the motor speed control circuit 536 may control the voltage and frequency applied to the electric motor 534. In the case of a DC motor, the motor speed control circuit 536 may control the DC voltage applied to the electric motor 534. In the case of a stepper-motor, the motor speed control circuit 536 may control the current flowing to the poles of the motor, but the stepper-motor may have a sufficient number of poles, or is controlled in such a way, that the rotor 124 moves smoothly.

The processor 500 couples to the motor speed control circuit 536, such as by way of the digital-to-analog converter 506 (as shown by bubble C). The processor 500 may be coupled in other ways as well, such as packet-based communication over the communication port 512. Thus, the processor 500, running a program, may read electrical current supplied on the active terminal 518, may read voltage supplied on the active terminal 518, and responsive thereto may make speed control changes (and thus volume flow rate changes) by sending speed commands to the motor speed control circuit 536. The motor speed control circuit 536, in turn, implements the speed control changes. Speed control changes may comprises changes in speed of the rotor 124 when desired, stopping the rotor 124 when desired, and in some embodiments temporarily reversing the rotor 124. Before proceeding it is noted that the rotor 124 of the peristaltic pump need not be turned by an electric motor. While an electric motor may be easier to implement in an electrical-based control system, other types of motors for which speed of the output shaft can be controlled (e.g., pneumatic motors) may be equivalently used.

The specification now turns to a more detailed description of the various modes of operation that may be implemented by the electrosurgical system. Each mode of operation is illustratively named based on the aggressiveness of the ablation. However, all the illustratively identified tissue types may be ablated in each and every mode, and thus providing an indication of the type of tissue expected to be ablated in each mode shall not be read as a limitation of the applicability of any particular mode. Ablating tissue in a mode not specifically designed for the tissue may result unwanted effects, such as discoloration or removal of too much of the target tissue. The available modes of operation of the system thereby provide enhanced performance where the management of energy output in conjunction with control of aspiration flow rates creates surgical results in each mode that are tuned to the targeted tissue or type of surgical procedure.

In accordance with the various embodiments, the electrosurgical controller 100 implements at least two, and in some embodiments four, modes of operation to modulate the flow rate dynamically in the vicinity of an active electrode in order to regulate the output of RF energy: a "low mode" which may be used for treatment, ablation, and removal of portions of cartilage; a "medium mode" which may be used for treatment, ablation, and removal of meniscus; a "high mode" which may be used for aggressive ablation and removal of tissue; and a "vacuum mode" for removal free floating and/or trapped tissue. Each illustrative mode of operation may be characterized by an initial energy setting for the voltage generator 516 and an initial volume flow rate by the peristaltic pump 118, which initial settings may result in a particular desired impedance of the plasma created during ablation. During operation within a particular mode, the energy provided by the voltage generator 516 and volume flow rate provided by the peristaltic pump 118 may change based on operational conditions at the distal end 108 of the wand, but such changes shall not obviate the status of being within a particular operational mode. The following table characterizes at a high level the four illustrative operational modes.

TABLE 1

| Low Mode | Medium Mode | High Mode | Vacuum Mode |
| --- | --- | --- | --- |
| Low energy to active electrode. Low aspiration flow. | Medium energy to active electrode. Medium aspiration flow. | High energy to active electrode. High aspiration flow. | Low to High energy to active electrode. Very high or pulsed aspiration flow. |

Each mode will be discussed in turn.

The low mode of operation is designed specifically for the treatment and selective ablation of articular cartilage or other very sensitive tissue. This low mode of operation is particularly appropriate for chondroplasty and meniscus finishing or sculpting. However, cartilage does not grow back, and thus the amount of cartilage ablated by a surgeon during a chondroplasty procedure is in most procedures very small. The primary concern of the surgeon may be to carefully remove diseased cartilage while at the same time reducing the damage to the chondral tissue that remains. For these reasons, the illustrative low mode is characterized by low energy provided to the active electrode, as well as low volume flow rate for the aspiration. In particular, in this mode of operation energy delivery during treatment is desired to maximize cell viability and to create reduced instantaneous energy dissipation and heat production in the vicinity of the treatment site. The reduced suction flow and low volume flow rate associated with this mode of operation may result in a plasma and electrode circuit having a higher overall impedance.

Vapor layer collapse and short spike of current are avoided if possible in the low mode, and thus volume flow rate control in the low mode may implement aggressive control action with respect to slowing the volume flow rate (i.e., decreases in speed of the rotor 124 of the peristaltic pump 118) in order to maintain the efficacy and stability of the plasma. In some cases, the control action may result in momentary reversals of direction of the rotor 124 of the peristaltic pump 118. Reversal of the rotor 124 of the peristaltic pump 118 may not result in reverse volume flow rate at the active electrode 202 (taking into account elasticity of the tubing 116), but nevertheless may enable the controller 104 to quickly slow or stop the volume flow rate at the active electrode when the controller 104 senses the plasma is collapsing. In order to reduce thermal damage to surrounding tissue, in the low mode it may be desirable to reduce aspiration volume flow to substantially zero while the RF energy is activated. The control action would then provide for a baseline aspiration volume flow rate when the RF is deactivated in order to remove loose tissue bodies and to evacuate bubbles from the surgical field to improve visualization.

With respect to the voltage generator 516, the low mode is characterized by low energy, and in some embodiments the controller 104 implements an upper limit on the amount of energy provided to the active electrode 202. For a voltage generator 516 that produces constant RMS voltage, the amount of current provided to the active electrode 202 may be controlled. For a voltage generator 516 that controls voltage output, both the RMS voltage and RMS current may be controlled to implement low energy delivery.

In the low mode of operation, the controller 104 controls the voltage generator 516 and peristaltic pump 118 to implement relatively high target impedance for the plasma and electrode circuit, and to avoid plasma collapse. Control action in response to decreasing impedance (as calculated based on the current and/or voltage applied to the active electrode) may involve both lowering the energy supplied by the voltage generator 516 and slowing and/or stopping the peristaltic pump 118. In some embodiments, changes in the electrical energy produced by the voltage generator 516 may be implemented more quickly than changes in peristaltic pump 118 speed, and thus in some embodiments an initial reaction to measured decreasing plasma impedance may be momentarily increasing the level of supplied energy, followed by decreasing pump speed and lowering again the supplied energy.

The medium mode of operation is designed specifically for ablation of fibro-cartilaginous tissue like meniscal tissue, but other types of tissue may also be ablated in the medium mode. This medium mode of operation may also be appropriate for the electrosurgical treatment of labrum tissue. When ablating meniscus, the surgeon may be interested in ablating more tissue volume than with respect to cartilage, but any resulting oxidation or "browning" of the remaining meniscus is disfavored. For at least this reason, the illustrative medium mode is characterized by medium energy provided to the active electrode, as well as medium volume flow rate of the aspiration in order to preserve tissue consistency. In particular, in this mode of operation energy delivery during treatment is desired to increase tissue matrix preservation and to prevent tissue matrix alteration with reduced or no tissue discoloration, or cross-linking of the collagen fibers that could result in mechanical alterations. The medium volume flow rate may result in a plasma that has a lower impedance than the low mode along with relatively little heat dissipation in the area of the treatment site.

Plasma collapse is disfavored in the medium mode, but occasional plasma collapse and short current spikes may be tolerated to implement the slightly more aggressive tissue ablation rate. Thus, control action with respect to the volume flow rate in the meniscus mode may be more aggressive than the low mode, and a minimum volume flow rate for the aspiration may be implemented, even if such minimum results in plasma collapse.

With respect to the voltage generator 516, the medium mode is characterized by slower changes responsive to variations in impedance of the plasma. For a voltage generator 516 that produces constant peak voltage, the amount of current provided to the active electrode 202 may be averaged and controlled to provide a predetermined average current. For a voltage generator 516 that controls voltage output, the average energy may be controlled.

In the medium mode of operation, the controller 104 controls the voltage generator 516 and peristaltic pump 118 to implement a medium target impedance for the plasma electrode circuit. Control action in response to decreasing impedance (as calculated based on the current and/or voltage applied to the active electrode) may involve both changing the energy supplied by the voltage generator 516 and slowing and/or stopping the peristaltic pump 118. In some embodiments, the controller 104 may provide predetermined energy, and for impedance values falling within a predetermined range, the controller 104 may control impedance based solely on changes in speed of the peristaltic pump 118. For variations in impedance that fall outside with a predetermined range, the control strategy may also rely on changes in energy supplied by the voltage generator 516.

The illustrative high mode of operation is designed specifically for quickly removing tissue. By way of example, this high mode of operation may be used for sub-acromial decompression treatments or ACL stump debridement. For this reason, the illustrative high mode is characterized by high energy provided to the active electrode, as well as high volume flow rate for aspiration. In particular, in this mode of operation energy delivery during treatment is adjusted for increased tissue removal with continuous aspiration flow volume to pull tissue closer to the wand for more efficient ablation rates and for reduced heat dissipation. The high volume flow rate will result in plasma having lower impedance, and regular (but uncontrolled) plasma collapse. Thus, plasma collapse is expected in the high mode based on the aggressive aspiration flow, but the high mode may implement a minimum volume flow rate, and thus a minimum peristaltic pump speed, even if such minimum speed results in plasma collapse.

With respect to the voltage generator 516, the high mode is characterized by slower changes responsive to variations in impedance of the plasma. Changes in energy provided to the wand electrode may be implemented slowly, but with the voltage generator 516 quickly throttling energy, or shutting off completely, when a predetermined high energy level is reached (e.g., over two Amps). For a voltage generator 516 that produces constant RMS voltage, the amount of current provided to the active electrode 202 may be controlled to a predetermined amperage. For a voltage generator 516 that controls voltage output, the average power may be controlled.

In the high mode of operation, the controller 104 controls the voltage generator 516 and peristaltic pump 118 to implement low target impedance for the plasma. Control action in response to decreasing impedance (as calculated based on the current and/or voltage applied to the active electrode) may involve slowing the peristaltic pump 118, but only to predetermined minimum volume flow rate. In some embodiments, the controller 104 may provide predetermined energy, and for impedance values falling within a predetermined range, the controller 104 may control impedance based solely on changes in speed of the peristaltic pump 118. For variations in impedance that fall outside a predetermined range, the control may also rely on changes in energy supplied by the voltage generator 516.

Plasma collapse is expected, yet in the high mode the precise timing of plasma collapse is uncontrolled. In a particular embodiment, the controller 104 aggregates or counts an amount of time that a plasma exists proximate the active electrode, and also the total time (over any suitable period, such as a one second). For example, the controller may assume that at times when current is below a predetermined threshold (e.g., 500 milli-Amps) that plasma exists (as higher current will flow when in the absence of the impedance associated with the plasma). Responsive to the aggregated time in the plasma mode, the controller 104 may determine a value indicative of the "duty cycle" of the plasma to non-plasma times, such as by taking a ratio time when plasma is present to total time in the period. If the value indicative of the duty cycle indicates operation outside the plasma mode more than a predetermined amount (e.g., less than 25% of the time), control changes may be made, like decreasing the aspiration flow rate.

The illustrative vacuum mode of operation is designed specifically for quickly removing loose tissue and tissue fragments within the surgical field. For this reason, the illustrative vacuum mode is characterized by variable energy provided to the active electrode, as well as the highest volume flow rate as between the various modes (when the aspiration is active). In particular, in this mode of operation energy delivery during treatment is desired to be optimized for fast digestion of debris within the surgical field in conjunction with a high volume flow rate in order to attract debris to the wand tip. The high volume flow rate will result in plasma having lower impedance.

Plasma collapse is expected in the vacuum mode based on the aggressive volume flow rate for the aspiration. In some cases the flow rate volume will be set and remain unchanged throughout use of the mode. In other cases, the vacuum mode may implement pulsed volume flow rate, alternating between the highest volume flow rate for aggressive tissue removal, and a lower volume flow rate to enable an extinguished plasma to "re-ignite." For example, in one illustrative pulsating flow embodiment the higher volume flow rate may be implemented for 0.5 seconds, and then the lower volume flow rate implemented for 0.5 seconds. Other times are possible, with the higher volume flow rate ranging from between 0.1 and 1.0 seconds, and the lower volume flow rate ranging from between 0.1 and 1.0 seconds. Moreover, the times as between the higher volume flow rate and the lower volume flow rate need not be balanced.

With respect to the voltage generator 516, the vacuum mode is characterized by slower changes responsive to changes in impedance of the plasma and electrode circuit. Changes in energy provided may be implemented slowly, but with the voltage generator 516 quickly throttling energy, or shutting off completely, when a predetermined high energy level is reached (e.g., over two amps). For a voltage generator 516 that produces constant peak voltage, the amount of current provided to the active electrode 202 may be controlled to a predetermined amperage. For a voltage generator 516 that controls voltage output, the average power may be controlled.

In the vacuum mode of operation, the controller 104 may not make operative control changes (other than implementing the pulsating aspiration flow). In other words, changes in impedance of plasma may not result in changes in set point current and/or energy provided to the voltage generator 516 by the processor 500. In other cases, changes in energy delivery are slower than the other modes of operation, with occasional reductions at and/or shut down of energy associated with a predetermined high energy flow.

Figure 6:
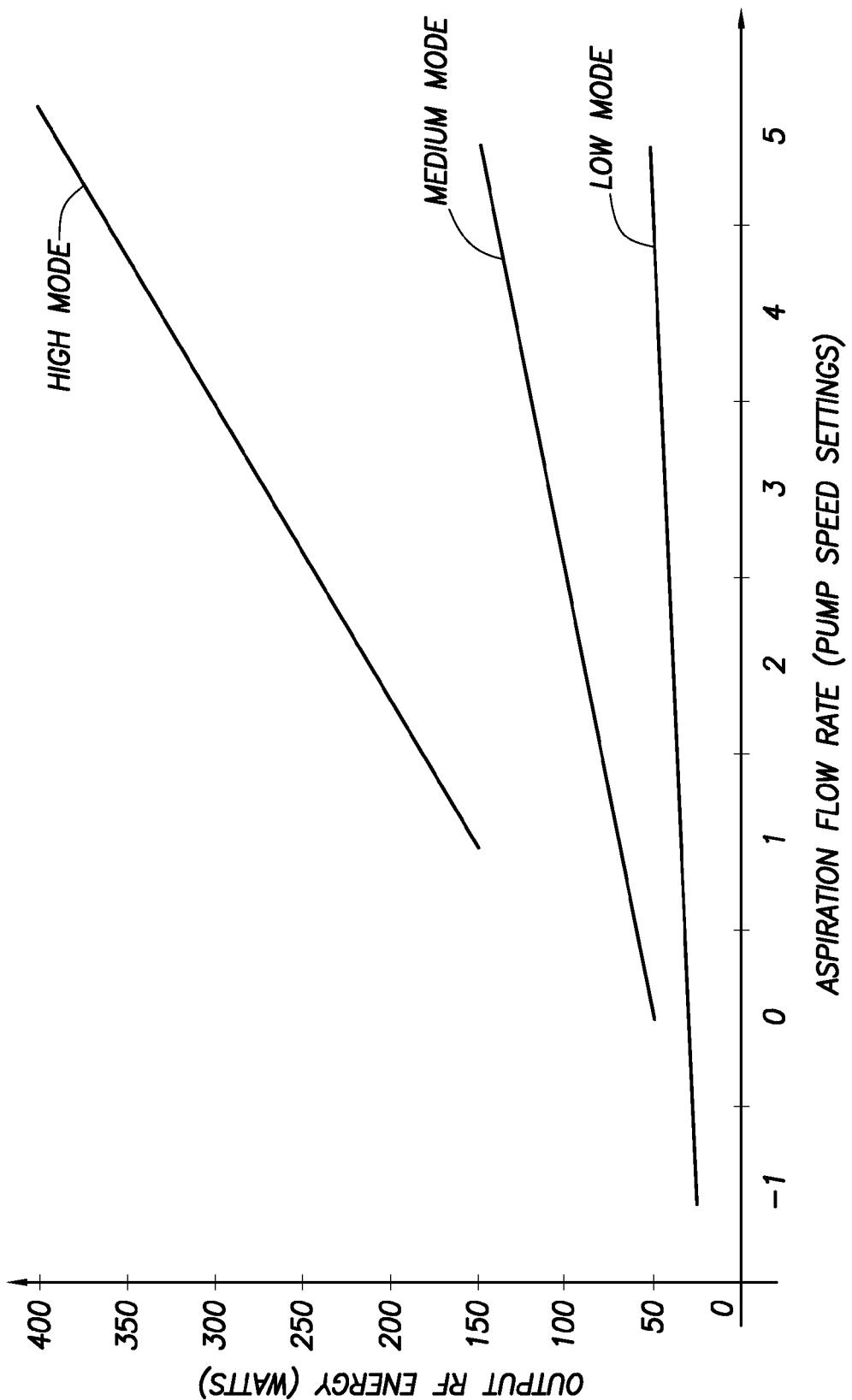
FIG. 6 shows an example graph relating output RF energy and aspiration flow of various modes in accordance with at least some embodiments.

FIG. 6 shows a graph that relates possible ranges of output RF energy to aspiration flow rate (shown as pump speed settings) for three example operational modes—low mode, medium mode, and high mode. In particular, for each mode of operation the electrosurgical controller 104 is programmed to operate within a range of operational parameters associated with output RF energy and aspiration flow rate. For example, in the "low mode" of operation described above, controller 104 may be pre-programmed to allow output RF energy only in a range from 25-50 Watts, and aspiration flow rates set points from an example "−1" (i.e., reverse motor direction) to "5", which in some cases may result in an aspiration flow in a range from 0-45 ml/min. For the example "medium mode" of operation described above, controller 104 may be pre-programmed to allow output RF energy only in a range from 50-150 Watts, and aspiration flow rates set points from an example "0" (i.e., peristaltic motor stopped) to "5". For the example "high mode" of operation described above, controller 104 may be pre-programmed to allow output RF energy only in a range from 150-400 Watts, and aspiration flow rates set points from an example "1" to "5".

Though each mode may be characterized by particular energy and volume flow rate, to help initially establish plasma, the volume flow rate may initially be lower, and likewise the voltage of the applied energy may be lower, to help establish a gas phase of the fluid near the active electrode. Moreover, and again regardless of mode of operation, once plasma has been created at a lower volume flow rate and applied voltage, the ramping of the voltage and volume flow rate to the initial set points for the mode of operation may be synchronized. In accordance with at least some embodiments, the voltage generated 516 is configured to limit or interrupt current flow when low resistivity material (e.g., blood, saline or electrically conductive gel) causes a lower impedance path between the return electrode(s) and the active electrode(s). Further still, in some embodiments the voltage generator 516 is configured by the user to be a constant current source (i.e., the output voltage changes as function of the impedance encountered at the wand 102).

The above discussion is meant to be illustrative of the principles and various embodiments of the present invention. Numerous variations and modifications are possible. It is intended that the following claims be interpreted to embrace all such variations and modifications. For example, while FIG. 6 shows non-overlapping output RF energy as between the example modes of operation, the ranges are merely examples. In other situations the output RF energy of the operational modes may overlap (e.g., the output RF energy of the lower end of the medium mode may overlap with the output RF energy of the upper end of the low mode). Thus, the specification should not be read to require that the various example operational modes require mutually exclusive output RF energy ranges.

Figure 7:
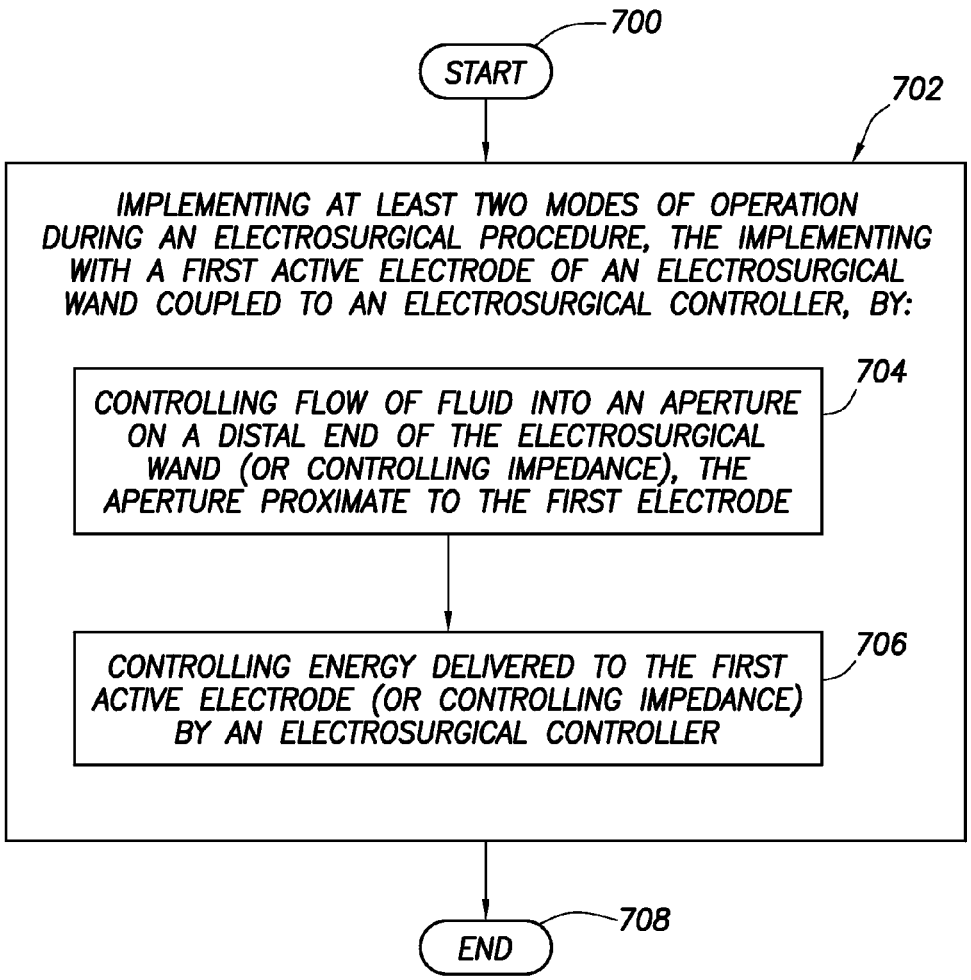
FIG. 7 shows a method in accordance with at least some embodiments.

Fig. 7 is a block diagram, describing a method which may start (block 700) and comprise: implementing at least two modes of operation during an electrosurgical procedure, the implementing with a first active electrode of an electrosurgical wand coupled to an electrosurgical controller (block 702), the implementing by: either controlling flow of fluid into an aperture on a distal end of the electrosurgical wand, the aperture proximate to the first electrode or by controlling the impedance of an electrode circuit (block 704); and either controlling energy delivered to the first active electrode by an electrosurgical controller or controlling impedance of the electrode circuit (block 706). The method may then end (block 708).

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical controller comprising:
    a processor;
    a memory coupled to the processor;
    a voltage generator operatively coupled to the processor, the voltage generator comprising an active terminal;
    a wand connector configured to couple to a connector of an electrosurgical wand, and the wand connector comprising a plurality of electrical pins, and at least one electrical pin coupled to the active terminal of the voltage generator;
    a peristaltic pump comprising a rotor coupled to an electric motor, the electric motor operatively coupled to the processor;
    wherein the memory stores a program that, when executed by the processor, causes the processor to:
        implement a first mode of ablation by setting a first predetermined speed of the rotor of the peristaltic pump and by setting a first predetermined energy provided by the voltage generator; and
        implement a second mode of ablation by setting a second predetermined speed of the rotor of the peristaltic pump and by setting a second predetermined energy provided by the voltage generator, the second predetermined speed different than the first predetermined speed, and the second predetermined energy different than the first predetermined energy.

2. The electrosurgical controller of claim 1 further comprising an outer enclosure, wherein the processor, memory, voltage generator, wand connector and peristaltic pump are at least partially disposed within the outer enclosure.

3. The electrosurgical controller of claim 1 further comprising:
    a first outer enclosure, wherein the processor, memory, voltage generator, and wand connector are at least partially disposed within the outer enclosure; and
    a second outer enclosure distinct from the first outer enclosure, wherein the peristaltic pump is at least partially disposed within the second outer enclosure.

4. The electrosurgical controller of claim 1 wherein the program, during each mode of ablation, further causes the processor to:
    adjust the speed of the rotor of the peristaltic pump responsive to changes in a parameter indicative of impedance of the electrode circuit; and
    adjust energy provided by the generator responsive to changes in the parameter indicative of impedance of electrode circuit.

5. The electrosurgical controller of claim 4 wherein when the processor adjusts the speed of the rotor, the program further causes the processor to at least one selected from the group consisting of: momentarily stop the rotor; and momentarily reverse the rotor direction.

6. The electrosurgical controller of claim 1 wherein the first mode of ablation and the second mode of ablation are each selected from the group consisting of: a low mode for use ablating cartilage; a medium mode for use ablating fibrocartilage; a high mode for ablating soft tissue; and a vacuum mode for removal of free floating tissue.

7. The electrosurgical controller of claim 1 wherein the program further causes the processor to implement a third mode of ablation by setting a third predetermined speed of the rotor of the peristaltic pump and by setting a third predetermined energy provided by the voltage generator, the third predetermined speed different than the first and second predetermined speeds, and the third predetermined energy different than the first and second predetermined energy.

8. The electrosurgical controller of claim 7 wherein first, second and third modes of ablation are each selected from the group consisting of: a low mode for use ablating cartilage; a medium mode for use ablating fibro-cartilage; a high mode for ablating soft tissue; and a vacuum mode for removal of free floating tissue.

9. A system comprising:
an electrosurgical controller comprising
a processor;
a memory coupled to the processor;
a voltage generator operatively coupled to the processor, the voltage generator comprising an active terminal;
a wand connector configured to couple to a connector of an electrosurgical wand, and the wand connector comprising a plurality of electrical pins, and at least one electrical pin coupled to the active terminal of the voltage generator;
a peristaltic pump comprising a rotor coupled to an electric motor, the electric motor operatively coupled to the processor;
an electrosurgical wand comprising
an elongate shaft that defines a proximal end and a distal end;
a first active electrode disposed on the distal end of the elongate shaft;
a connector comprising at least one pin, the at least one pin electrically coupled to the first active electrode;
wherein the memory stores a program that, when executed by the processor, causes the processor to implementing at least two modes of ablation during an electrosurgical procedure, the implementing with the first active electrode of the electrosurgical wand;
wherein when the program implements the at least two modes, the program causes the processor to:
control impedance of an electrode circuit during a first mode of ablation of an electrosurgical procedure; and then
control impedance of the electrode circuit during a second mode of ablation of the electrosurgical procedure, the impedance of the electrode circuit during the second mode different than the impedance of the electrode circuit during the first mode.

10. The system of claim 9 wherein when the processor controls the impedance of the electrode circuit during the first mode of ablation, the program causes the processor to:
control flow of fluid into an aperture on the distal end of the electrosurgical wand, the aperture proximate to the first active electrode; and
control energy delivered to the first active electrode by the electrosurgical controller.

11. The system of claim 10 wherein when the processor controls the impedance of the electrode circuit during the second mode of ablation, the program causes the processor to:
control flow of fluid into the aperture, the flow of fluid in the second mode different than the flow of fluid in the first mode; and
control energy delivered to the first active electrode, the energy delivered to the first active electrode in the second mode different than the energy delivered to the first active electrode in the first mode.

12. The system of claim 10 wherein when the processor controls the flow of fluid into the aperture, the program causes the processor to control speed of the rotor of the peristaltic pump.

13. The system of claim 12 wherein when the processor controls the speed of the rotor of the peristaltic pump, the program further causes the processor to momentarily reverse direction of the rotor of the peristaltic pump.

14. The system of claim 9 further comprising:
a first outer enclosure, wherein the processor, memory, voltage generator, and wand connector are at least partially disposed within the outer enclosure; and
a second outer enclosure distinct from the first outer enclosure, wherein the peristaltic pump is at least partially disposed within the second outer enclosure.

15. The system of claim 9 wherein the program, during each mode of ablation, further causes the processor to:
adjust a speed of the rotor of the peristaltic pump responsive to changes in a parameter indicative of impedance of the electrode circuit; and
adjust energy provided by the generator responsive to changes in the parameter indicative of impedance of the electrode circuit.

16. The system of claim 15 wherein when the processor adjusts the speed of the rotor, the program further causes the processor to at least one selected from the group consisting of: momentarily stop the rotor; and momentarily reverse the rotor direction.

17. The system of claim 9 wherein the at least two modes of ablation are selected from the group consisting of: a low mode for use ablating cartilage; a medium mode for use ablating fibro-cartilage; a high mode for ablating soft tissue; and a vacuum mode for removal of free floating tissue.

* * * * *